United States Patent [19]

DeLeo

[11] 4,144,876
[45] Mar. 20, 1979

[54] HAIR IMPLANTING METHOD

[76] Inventor: David B. DeLeo, 126 Sturges Rd., Wilton, Conn. 06897

[21] Appl. No.: 862,767

[22] Filed: Dec. 20, 1977

[51] Int. Cl.² .............................................. A61B 17/00
[52] U.S. Cl. .......................................... 128/1 R; 3/1; 128/330
[58] Field of Search ....................... 128/330, 329, 1 R; 3/1; 132/5

[56] References Cited

U.S. PATENT DOCUMENTS

| 1,059,631 | 4/1913 | Popovics | 128/330 |
| 3,596,292 | 8/1971 | Erb | 128/330 X |
| 3,858,245 | 1/1975 | Nate et al. | 128/329 X |
| 3,998,230 | 12/1976 | Miller | 128/330 |

*Primary Examiner*—Robert W. Michell
*Assistant Examiner*—Michael H. Thaler

*Attorney, Agent, or Firm*—H. Gibner Lehmann; K. Gibner Lehmann

[57] ABSTRACT

An apparatus and method of implanting hair or hair-like strands in areas of the skin of animate beings, comprising a unique fabricated anchorage piece and a novel process for placing the same in the skin, utilizing a hypodermic needle having a grooved barrel and tip portion. The process or method comprises piercing the skin with the assemblage of needle and anchorage member carried thereby, and then advancing the member by means of a suitable plunger in the needle, such that the member is thrust below the surface of the skin while the needle tip is still inserted. The needle is then withdrawn, whereas the anchorage member remains embedded. Strands of hair or hair-like material tied or otherwise secured to the anchorage member emanate from the puncture in the skin created by the needle, thereby providing an especially natural and pleasing appearance not obtainable with most prior methods and procedures of hair replacement.

8 Claims, 9 Drawing Figures

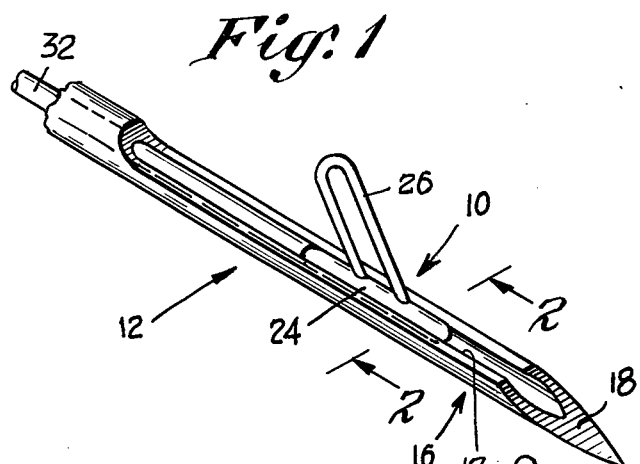
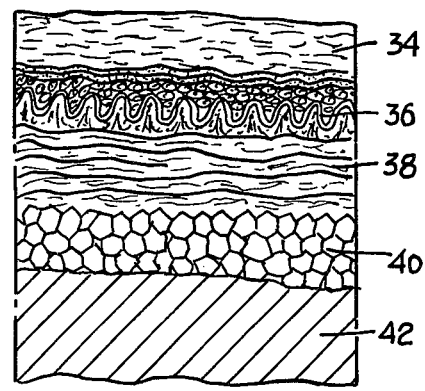
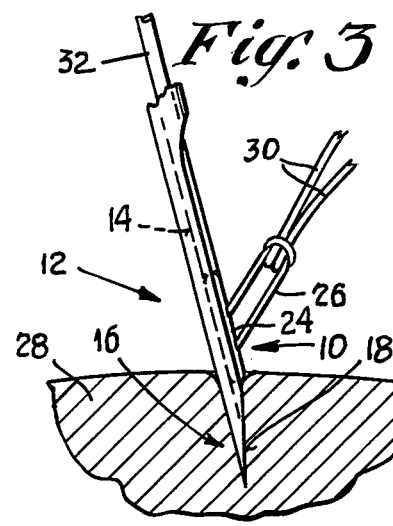
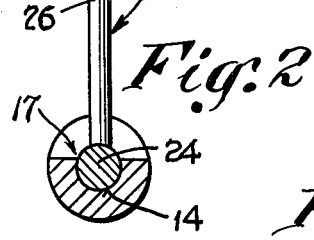
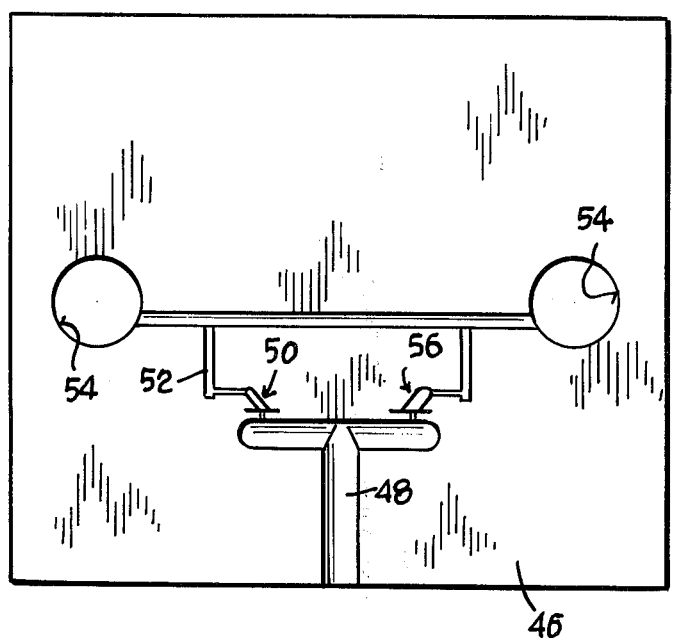
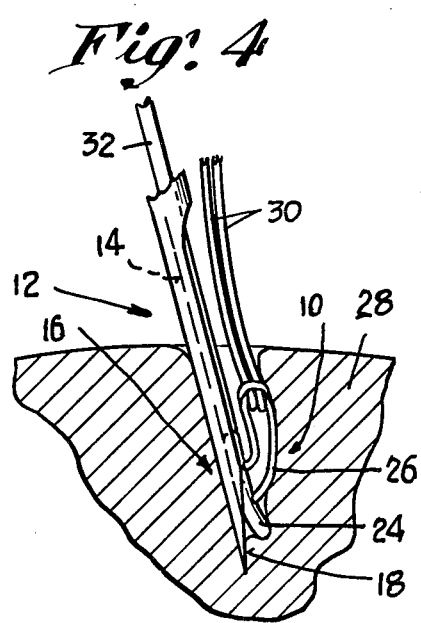

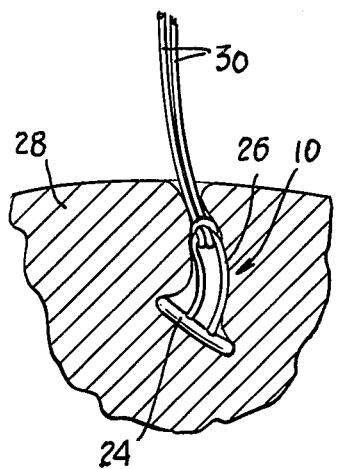
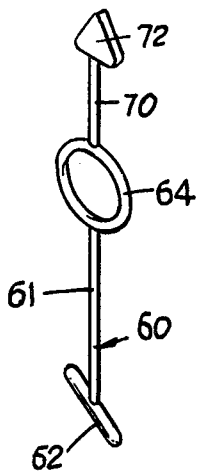
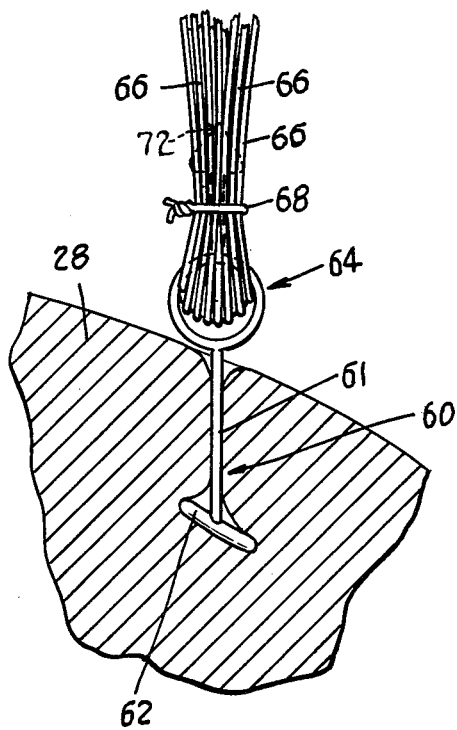

HAIR IMPLANTING METHOD

BACKGROUND

This invention relates generally to methods of hair replacement, and more particularly to the method for implantation of small structural anchorage members into the skin, having hair or hair-like strands secured thereto.

Many different techniques and devices for hair replacement have been proposed and produced over the years, only some of which have met with any substantial degree of success. Most past methods were generally limited to wigs or hairpieces intended to be affixed to the scalp either with tape or adhesives. More recently the use of inert sutures adapted to be permanently implanted into the scalp has found some acceptance. A method disclosing one such arrangement is found in U.S. Pat. No. 3,858,245.

Still other methods involved the securing of a hairpiece directly to the subject's own hair by a process known as hair weaving. These methods, however, have met with limited success because a re-weave was of necessity required every few months in order to compensate for the loosening of the hairpiece as the subject's natural hair grew and lengthened. The above requirement represented a distinct inconvenience and drawback to the wearer, as well as involving additional periodic costs which were burdensome.

In addition to the foregoing disadvantages, the results obtained by the suture implant and hair-weaving techniques mentioned above were in general less than satisfactory since the appearance of a natural hairline was not readily achieved.

In still other methods, individual hairs were implanted directly into the skin. Such arrangements are disclosed in U.S. Pat. Nos. 3,596,292; 4,004,592; and 3,119,398. Many of these prior patented techniques proved to be unsuccessful because either the hairs tended to fall out or to be pulled out easily, or else could not be readily replaced in the event that the hair filaments either wore out, or that their coloring became bleached out for some reason. In certain cases, the material of implanted hair-like strands was incompatible with living tissue, causing problems with either infection or else rejection of the irritating substance by the body.

SUMMARY

The above disadvantages and drawbacks of prior hair replacement devices and procedures are obviated by the present invention, which has for one object the provision of a novel and improved method of hair replacement which is especially simple to produce and carry out, which minimizes the problems of infection or tissue rejection, and which provides an appearance that is much more natural than was previously possible, particularly along the hair line.

A related object of the invention is the provision of an improved method as above set forth, which permits the strands of hair or hair-like material to be readily replaced at a later time, should the occasion ever arise, as a result of wear, breakage, or bleach-out of coloring.

Yet another object of the invention is the provision of an improved method as above characterized, wherein the implantation can be carried out in a minimum of time and with the least inconvenience to the subject.

Still another object of the invention is the provision of an improved method which greatly reduce the likelihood of rejection, by virtue of the use of improved inert materials which have been found to cause little or no irritation to the tissues of the body.

The above objects are accomplished by the provision of a novel method of implanting a unique hair anchorage member either with or without attached hair or hair-like strands, in areas of the skin. The method comprises the steps of placing the anchorage member in a hypodermic needle having a grooved barrel portion and tip, and piercing the skin with the assemblage of needle and member carried thereby, then advancing the member further into the skin by means of a suitable plunger carried by the needle, whereby the anchorage member is thrust forward and below the surface of the subject's skin while the tip portion of the needle is still below the surface. Thereafter the needle is carefully withdrawn, allowing the anchorage member to remain embedded. Strands of hair or hair-like material are tied or otherwise secured to the anchorage member preferably before the latter is embedded, so as to emanate from the puncture in the skin created by the needle.

In a second embodiment of the invention, there is provided an anchorage member which has a loop portion adapted to project slightly from the surface of the skin, thereby to enable strands of hair or hair-like substance to be secured to the exposed part after the member is embedded. A series of such members can be employed at the area which is to be covered. Since with the various embodiments of the invention the individual strands emanate essentially directly from the skin surface, a very natural appearance is realized, thereby overcoming one of the disadvantages of virtually all prior devices and methods of hair replacement.

Other features and advantages will hereinafter appear.

In the accompanying drawings, illustrating various embodiments of the invention and particularly the method provided by the invention:

FIG. 1 is a perspective view, greatly enlarged, of a hair or strand anchorage member of the invention as it is being carried by a special hypodermic needle having a slabbed-off side or grooved portion, the anchorage member being adapted for embedment under the surface of the skin of an animate being at a location where the hair or strand is to be added.

FIG. 2 is a transverse section taken on the line 2—2 of FIG. 1.

FIG. 3 is a side elevational view, also greatly enlarged, of the needle and anchorage part as they have just begun to pierce the skin. The anchorage part, carried in the bore of the needle, is shown as having a single strand of hair or hair-like material secured to it.

FIG. 4 is a view like that of FIG. 3 except showing the needle and anchorage part as having penetrated more deeply into the skin. A plunger carried in the needle bore has been advanced slightly, forcing the anchorage member along the needle axis and partially out at the end of the needle such that the member will remain embedded in the skin.

FIG. 5 is an enlarged view like FIG. 4 except showing the needle removed, and wherein the anchorage member is retained below the surface of the skin with the strand of hair or hair-like substance emanating from said surface.

FIG. 6 is a diagrammatic, enlarged sectional representation (typical) of the various strata of a human scalp.

FIG. 7 is a top plan view, greatly enlarged, of a die suitable for molding one or more anchorage members of the type provided by the invention and employed with the method thereof.

FIG. 8 is a perspective view, greatly enlarged, of a somewhat modified anchorage member adapted to be employed with the method of the present invention, and FIG. 9 is an enlarged plan view of the anchorage member of FIG. 8, shown partially embedded beneath the skin surface and illustrating a number of strands of hair or hair-like substance secured thereto.

Referring first to FIGS. 1-5 and in accordance with the present invention there is provided a novel and improved method for implanting hair-like strands in areas of the human skin, employing a unique anchorage member or part 10 which is adapted to be embedded in the skin by means of a special open-bore needle that is generally designated by the numeral 12. The needle 12 is in the form of a metal tube, which has a cylindrical bore 14 fitted with an advanceable plunger 32, and has a grooved or slabbed-off tip portion 16 having a slot 17, which latter is adapted to provide clearance for a loop in the anchorage member 10 as will be described below. The end 18 of the tip portion 16 is bevelled off, as shown, in the usual manner in order to provide a sharp cutting or penetrating point. The width of the slot 17 is somewhat less than the diameter of the bore, to provide adequate retention for the member 10.

Referring particularly to FIGS. 1 and 2, the anchorage member 10 is seen to comprise integral parts capable of easy forming or molding, being constituted of an inert, tissue-compatible material such as Teflon (tetrafluorethylene) or Teflon-coated metal, or merely an inert metal such as stainless steel. In the case of a coated metal, the coating could be of a silicone substance, of Dacron, or of various polyolefins; alternately the member 10 can be entirely of resilient plastic substance, preferably molded. The member 10 includes a base or shouldered portion 24 which may be of cylindrical cross section so as to be slidably receivable in the groove of the tip portion 16 of the needle, and an upstanding tie portion or loop portion 26 which is preferably integral with the base portion 24 and has a suitable configuration for enabling one or more strands of hair-like material to be secured to it, as in the manner illustrated in FIG. 3 or otherwise. As shown particularly in FIG. 2, the bore of the grooved tip portion is semicylindrical, and in section extends through an arc slightly greater than 180°, such that the base portion 24 is held captive therein against lateral displacement, while still providing clearance for the upstanding tie portion 26. As can be readily understood, the base portion 24 of the anchorage member 10 is capable of free sliding movement along and out of the grooved tip portion 16 of the needle. Preferably the ends of the shouldered portion 24 are rounded, so as to minimize irritation of the surrounding tissues. In addition, the loop portion 26 is disposed at an acute angle with respect to the shouldered portion, to facilitate embedment into the skin, as will be described below.

Referring to FIG. 3 and in accordance with the present invention, with the anchorage member 10 carried by the tip portion 16 of the needle 12, the latter and the member are inserted as an assemblage into the scalp so as to pierce it, the scalp being designated by the numeral 28. FIG. 3 illustrates a strand 30 of hair or hair-like material which has been secured to the tie portion 26 of the member. As the needle 12 is being inserted, the tie portion 26 engages the surface of the skin of the scalp and is partially deformed and bent upwardly or back toward the base portion. The acute angle which the tie portion makes with the shouldered portion facilitates such bending, as can be readily understood. In addition, the cross sectional area of the filament making up the tie portion is preferably less than that of the shouldered portion, to enable such bending to occur. When the needle has been fully inserted to the position of FIG. 4, the plunger 32 is advanced along the needle bore 16, forcing the anchorage member 10 axially outward with respect to the needle. The latter is then withdrawn completely after the plunger 32 is further advanced, such that the anchorage member remains embedded in the scalp with the strand 30 emanating from the hole or passageway that was made by the needle. As the needle is withdrawn, the anchorage member assumes the position shown in FIG. 5. The skin surface fills in around the strand 30 at the point from which it emanates, and the appearance of one or more strands of hair growing out of the scalp is thus achieved. This is quite important, particularly at the hairline, since it enables the subject to have a completely normal and natural appearance.

FIG. 6 illustrates diagrammatically, in section, the various strata making up the scalp. In practice, the showings of FIGS. 3-5 would encompass the representation of FIG. 6. However, in the interest of simplicity, the scalp 28 in FIGS. 3-5 has been indicated by simple cross-hatching lines, in order to more clearly illustrate the implant procedure of the invention.

In FIG. 6, the numeral 34 indicates the stratum corneum; the layer 36 is the stratum germinativum, the layer 38 is the corium or dermis, and the numeral 40 indicates subcutaneous tissue. Osseous tissue (bone) is labelled 42 in FIG. 6.

As pointed out above, a number of different materials can be employed in fabricating an anchorage member similar to that shown in FIGS. 1-5. Where the member is to be molded of plastic, a die 46 similar to that shown in FIG. 7 can be used. This figure shows only a lower die half, the upper half being substantially a mirror image thereof. The die 46 includes an inlet port 48 through which molten plastic is introduced. The cavity for the anchorage member is designated by the numeral 50, and an air relief port 52 provides for the escape, from the cavity, of trapped gas during the molding process. The holes 54 receive corresponding positioning pins (not shown) on the upper die half, as can be readily understood. FIG. 7 also shows a second cavity 56 for forming a member having a slightly larger loop or tie portion, which may be more appropriate under certain circumstances or for certain applications.

Another embodiment of the invention is illustrated in FIGS. 8 and 9, showing a modified anchorage member 60 having a shaft 61 adapted to protrude partially from the scalp, a shouldered portion 62, and a loop portion 64 to receive multiple strands 66 of hair or hair-like substance. In carrying out the method of the invention, the shoulder portion 62 is placed in a hypodermic needle similar to that illustrated in FIG. 1, and is embedded in the scalp in the same manner as the anchorage member 10. In practice, the loop portion 64 is adapted to extend just slightly above the skin surface. The hair strands 66 may be secured to the loop portion after the shouldered portion is in position beneath the scalp surface. A ligature 68 is shown, having its ends twisted, for securing the strands to an upstanding extension 70 on the anchorage member. The extension may include an enlargement 72 at its end, for preventing the upward displacement of the ligature tie 68. Following embedment, the skin will surround the shaft 61 as shown in FIG. 9. The member 60 illustrated in FIGS. 8 and 9 is especially adapted to be employed at those areas of the scalp remote from the frontal portion or forehead, since it is desired that the loop portions 64 of the various members be camouflaged or hidden from view at all times. In other respects, the employment of the modified member 60 is substantially the same as that in the method of the first embodiment.

From the above it can be seen that I have provided a novel and improved method and means for hair replacement, involving impanting anchorage members in the skin and securing strands of hair or hair-like substance thereto, the method being both simple to carry out and effective in use, providing an especially natural and pleasing appearance to the subject. A substantial number of anchorage members can be employed, to give the coverage required in the area to be treated. With the novel apparatus described, minimum discomfort and inconvenience to the subject is involved, and the procedure can be carried out with a minimum of time, and with a minimum of complications. The method is thus seen to represent a distinct advance and improvement in the technology of hair replacements.

Each and every one of the appended claims defines a distinct aspect of the invention separate from the others, and each claim is accordingly to be treated in this manner when the prior art devices are examined in any determination of novelty or validity.

Variations and modifications are possible without departing from the spirit of the invention, and certain portions of the improvement may be used without others.

I claim:

1. The method of attaching an anchorage member for hair-like strands to an area of the skin, which comprises the steps of placing essentially the entire elongate base portion of an anchorage member in the bore of a hypodermic needle having a slot, and simultaneously placing a tie portion of said anchorage member in said slot whereby a major part of said tie portion lies substantially outside of the theoretical confines of the cylindrical outer surface of the needle and extends in directions generally transverse to the needle axis, piercing the skin with said needle, advancing the base portion of the anchorage member forwardly along said bore and simultaneously advancing said tie portion along the slot of the needle and into the skin so as to be embedded therein, the engagement with the skin of the said tie portion of the anchorage member causing a deformation of the same with respect to the base portion of the anchorage member so as to enable both portions to pass through the hole made by the needle with minimal enlargement of said hole, and thereafter removing the needle while allowing the base portion of the anchorage member to remain embedded in the skin.

2. The method as set forth in claim 1, and further including the step of attaching a strand of hair to the anchorage member.

3. The method as set forth in claim 2, wherein part of the tie portion of the anchorage member protrudes from the scalp, said method including the further step of attaching additional hair-like strands to said tie portion.

4. The method as set forth in claim 1, wherein the tie portion of the anchorage member comprises a loop which portrudes from the scalp, said method including the step of fastening a hair-like strand on said loop.

5. The method as set forth in claim 1, wherein the tie portion of the anchorage member comprises a loop, and wherein the step of advancing the anchorage member comprises embedding the loop below the surface of the scalp.

6. The method of claim 5, and further including the step of attaching a strand of hair to the loop.

7. The method of claim 6, wherein the step of piercing the skin creates a passageway from which the strand emanates, following removal of the hypodermic needle.

8. The method as set forth in claim 1, wherein the anchorage member tie portion comprises a loop and wherein the step of advancing said portions of the anchorage member comprises bending the loop toward the base portion as the member is embedded into the skin.

* * * * *